United States Patent [19]
Knighton et al.

[11] Patent Number: 6,071,232
[45] Date of Patent: *Jun. 6, 2000

[54] APPARATUS FOR VEIN REMOVAL

[75] Inventors: David R. Knighton, Minneapolis; Vance D. Fiegel, New Brighton, both of Minn.

[73] Assignee: Embro Vascular L.L.C., St. Louis Park, Minn.

[ * ] Notice: This patent is subject to a terminal disclaimer.

[21] Appl. No.: 09/107,158

[22] Filed: Jun. 29, 1998

Related U.S. Application Data

[63] Continuation of application No. 08/570,229, Dec. 11, 1995, Pat. No. 5,772,576.

[51] Int. Cl.$^7$ ............................................. A61F 2/04
[52] U.S. Cl. ............................................. 600/36; 600/104
[58] Field of Search ............................ 600/36, 104, 153; 623/1, 11–13

[56] References Cited

U.S. PATENT DOCUMENTS

| | | |
|---|---|---|
| Re. 29,088 | 12/1976 | Shaw . |
| 1,867,624 | 7/1932 | Hoffman . |
| 2,001,169 | 5/1935 | Wallace . |
| 2,011,169 | 8/1935 | Wappler . |
| 2,028,635 | 1/1936 | Wappler . |
| 2,316,297 | 4/1943 | Southerland et al. . |
| 2,868,206 | 1/1959 | Stoesser . |
| 2,944,552 | 7/1960 | Cannon . |
| 3,185,155 | 5/1965 | Slaten et al. . |
| 3,336,916 | 8/1967 | Edlich . |
| 3,856,016 | 12/1974 | Davis . |
| 3,882,854 | 5/1975 | Hulka et al. . |

(List continued on next page.)

FOREIGN PATENT DOCUMENTS

| | | |
|---|---|---|
| 3942589 | 7/1991 | Germany . |
| 112367 | 4/1957 | U.S.S.R. . |
| 510235 | 5/1976 | U.S.S.R. . |
| 1371689 A1 | 3/1986 | U.S.S.R. . |
| 2082459 | 3/1982 | United Kingdom . |
| 2195540 | 4/1988 | United Kingdom . |

OTHER PUBLICATIONS

DeLaria, "Leg Wound Complications Associated with Coronary Revascularization", *J. Thorac. Cardiovasc. Surg.*, 81:403–407, 1981.

Dmitri et al., "A quick and atraumatic method of autologous vein harvesting using the subcutaneous extraluminal dissector", *J. Cardiovasc. Surg.* 28:103–111 (1987).

Hauer et al., "Endoscopic subfacial discission of perforating veins", *Surgical Endosc.* 2:5–12 (1988).

Meldrum–Hanna et al., "Long Saphaneous Vein Harvesting", *J. Surg.* 56:923–924 (1986).

Rashid et al., "Subcutaneous Technique for Saphenous Vein Harvest", *Ann. Thorac. Surg.*, 372):169–170, 1984.

Wheatley, D.J., ed., *Surgery of Coronary Artery Disease*, C.V. Mosby Co., pp. 348–349, 374–375.

"Incision Decision", Atrium Medical Corporation advertisement, appearing in *J. Thorac. Cardiovasc. Surg.*, 83(4), 1982.

"Saphenous vein grafts are No. 1. Period.", Atrium Medical Corporation advertisement, appearing in *J. Thorac. Cardiovasc. Surg.*, 81(6), 1981.

Moazami et al., "Minimally Invasive Greater Saphenous Vein Harvesting for Coronary Artery Bypass Surgery", *Surgical Rounds*, pp. 94–98, Mar. 1997.

*Primary Examiner*—John P. Lacyk
*Attorney, Agent, or Firm*—Popovich & Wiles, PA

[57] ABSTRACT

A system for tissue harvesting comprising a tool to cut a vessel, apply a ligation clip, or remove patient's body fluids and a device for removing a generally cylindrical tissue structure such as a blood vessel from the body of a human or animal. The device includes a body portion having distal and proximal ends with at least one lumen extending longitudinally through the body portion. The lumen is sized to accommodate the vessel and at least one tool used in removing the vessel. Means is provided for isolating the vessel from the tools used in the removal procedure.

40 Claims, 11 Drawing Sheets

U.S. PATENT DOCUMENTS

| | | |
|---|---|---|
| 3,934,115 | 1/1976 | Peterson . |
| 4,362,160 | 12/1982 | Hiltebrandt . |
| 4,369,768 | 1/1983 | Vukovic . |
| 4,440,170 | 4/1984 | Golden et al. . |
| 4,556,058 | 12/1985 | Green . |
| 4,586,919 | 5/1986 | Taheri . |
| 4,638,802 | 1/1987 | Okada . |
| 4,653,476 | 3/1987 | Bonnet . |
| 4,745,908 | 5/1988 | Wardle . |
| 4,759,348 | 7/1988 | Cawood . |
| 4,759,364 | 7/1988 | Boebel . |
| 4,762,120 | 8/1988 | Hussein . |
| 4,768,508 | 9/1988 | Chin et al. . |
| 4,793,346 | 12/1988 | Mindich . |
| 4,858,595 | 8/1989 | Buess et al. . |
| 4,862,874 | 9/1989 | Kellner . |
| 4,869,268 | 9/1989 | Yoon . |
| 4,877,016 | 10/1989 | Kantor et al. . |
| 4,932,952 | 6/1990 | Wojciechowicz, Jr. . |
| 4,997,436 | 3/1991 | Oberlander . |
| 5,013,312 | 5/1991 | Parins et al. . |
| 5,020,514 | 6/1991 | Heckele . |
| 5,037,433 | 8/1991 | Wilk et al. . |
| 5,047,038 | 9/1991 | Peters et al. . |
| 5,213,093 | 5/1993 | Swindle . |
| 5,284,478 | 2/1994 | Nobles et al. . |
| 5,373,840 | 12/1994 | Knighton . |
| 5,425,355 | 6/1995 | Kulick . |
| 5,447,513 | 9/1995 | Davison et al. . |
| 5,549,637 | 8/1996 | Crainich . |

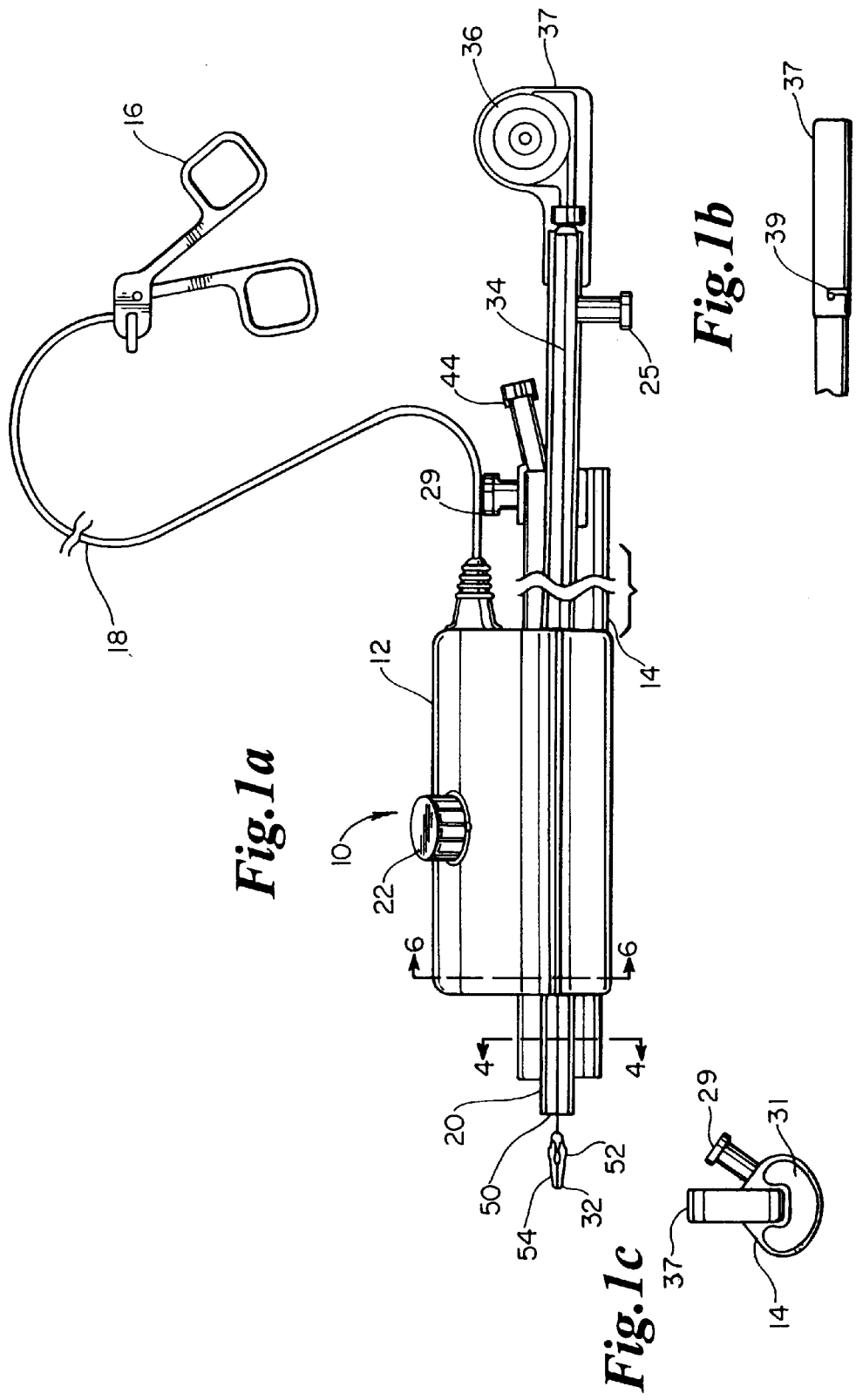

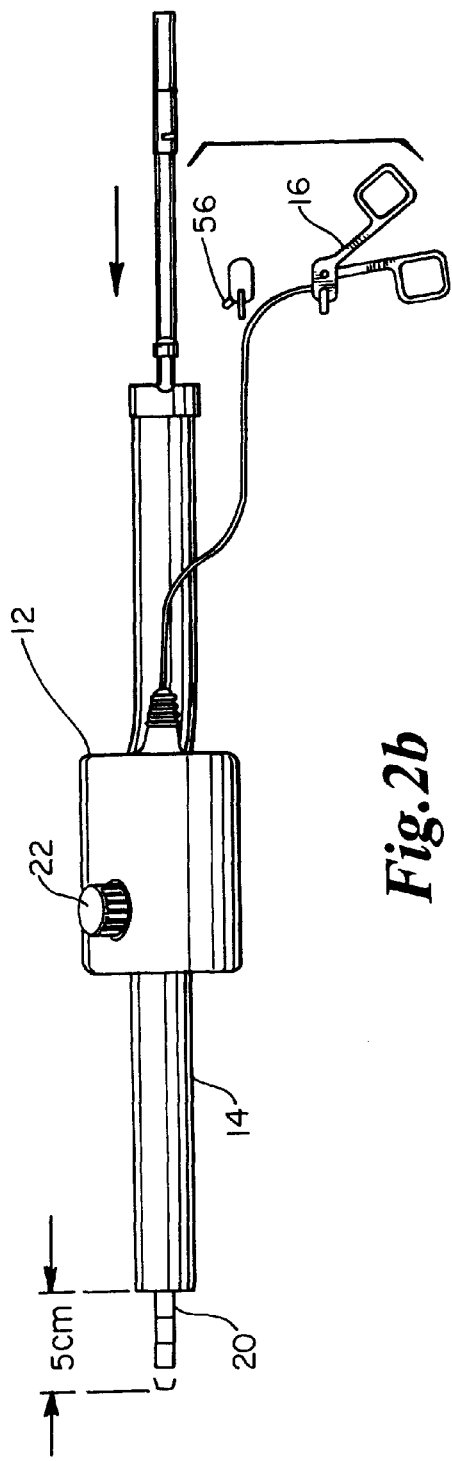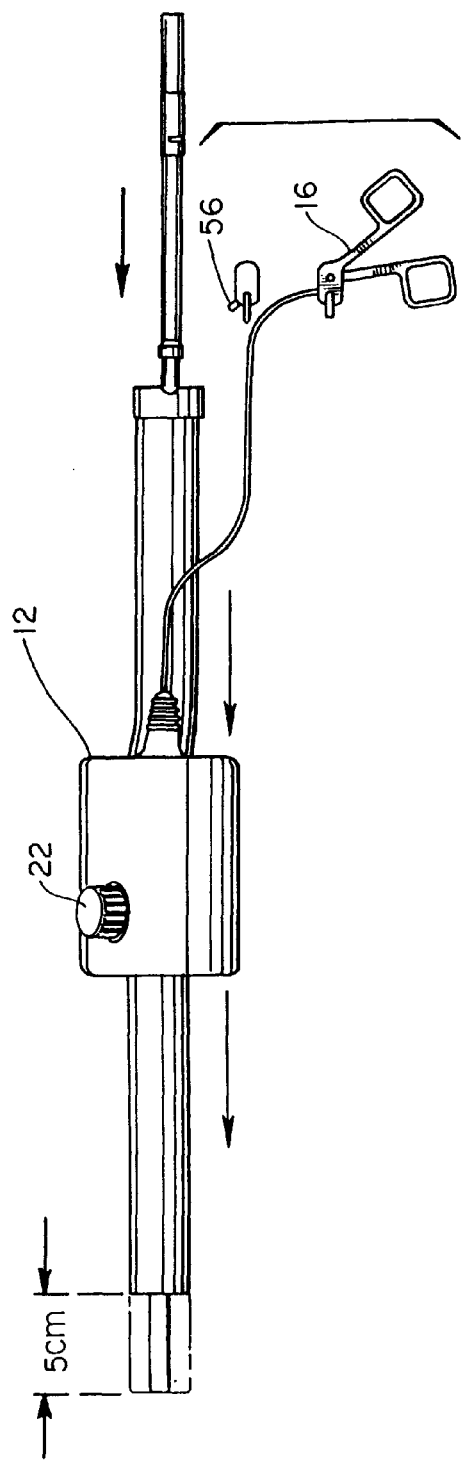

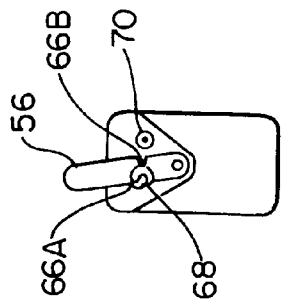
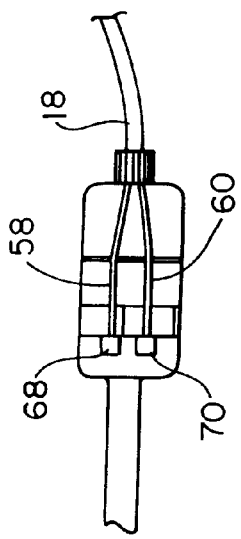
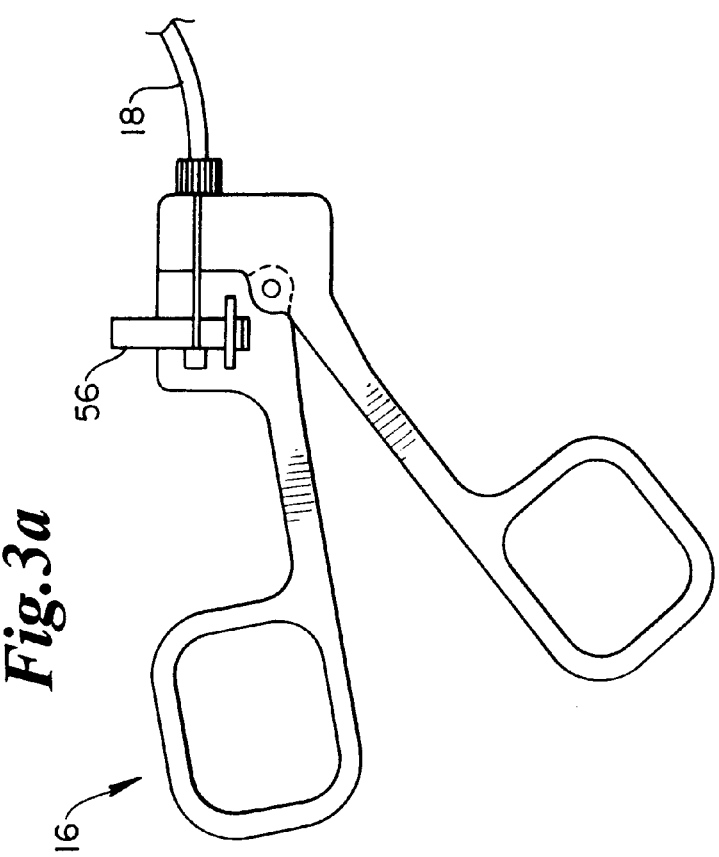

APPARATUS FOR VEIN REMOVAL

This is a continuation application of U.S. patent application Ser. No. 08/570,229 filed Dec. 11, 1995 now U.S. Pat. No. 5,772,576.

FIELD OF THE INVENTION

This invention relates to apparatus and methods used to harvest a generally cylindrical shaped tissue structure from the body of a patient. More particularly, the invention is directed to an apparatus and method for harvesting a section of a blood vessel from a patient.

BACKGROUND OF THE INVENTION

In certain circumstances it is desirable to remove sections of tubular tissue structure from a patient's body. Such tissue may be used in another part of the patient's body, may be transplanted into a second patient's body or may be discarded. As used herein, the term "tubular tissue structure" includes blood vessels, tendons, bile ducts and any other similar tissue formation which is generally tubular in structure and capable of being separated from surrounding tissue. Although the invention herein will be discussed in terms of harvesting blood vessels it should be understood that the apparatus and method described are equally applicable to harvesting other tubular tissue structure.

Vein harvesting is commonly done in connection with coronary artery bypass surgery. The saphenous vein is a subcutaneous vein which is often used for coronary artery bypass grafting, infra-inguinal bypass grafting and vein-vein bypass grafting. Other veins may also be used including the mammary vessel and the lessor saphenous vein. Previously, it has been necessary to make an incision along the full length of the vein section to be removed. The vein is then freed by severing and ligating the branches of the vein, after which the section of the vein can be removed from the patient. The full length incision must then be closed, for example by suturing or stapling. Obviously, the harvesting of the vein in this manner leaves disfiguring scars which are cosmetically undesirable. Additionally, the large incision creates a risk of infection to the patient and may not heal properly, especially with those patient's who have poor circulation in their extremities. Such an incision may create a chronic wound which will not heal.

Devices for harvesting a section of a blood vessel without creating a full length incision have been suggested. U.S. Pat. No. 4,793,346 to Mindich discloses a device for harvesting a section of a blood vessel by making only small incisions at opposite ends of the blood vessel section. The device includes a guide rod which fits inside of the vein section and a tube having an inner diameter slightly larger than the outer diameter of the vein section to be harvested. The tube has one or more knife blades at the leading edge which are connected to an electrical supply. The vein section is removed by making the incision sufficiently deep so as to expose the ends of the blood vessel to be harvested. The blood vessel is cut to expose one end, the guide rod is inserted inside the blood vessel section, and the tube is placed over the end of the blood vessel section to be removed. The tube is then pushed along the blood vessel (into the patient) while rotating the tube to sever the branches of the blood vessel with the knife blade mounted at the leading edge of the tube. Electrical current is supplied to the knife blades to heat the blades and thereby cauterize the ends of the severed branches of the blood vessel. The procedure is continued until the tube has reached the second of the two incisions. The blood vessel is exposed and cut from the patient at the second incision. The tube is then removed from the patient with the blood vessel section inside of the tube. The blood vessel section is then removed from the tube for further treatment and use as desired.

UK patent application GB 20 82 459A discloses a device for harvesting a section of a blood vessel similar to that disclosed in the Mindich patent. Again, two incisions are made, one at each end of the blood vessel section to be harvested. A guide rod is inserted into the blood vessel section through one of the incisions and a tube having a cutting element having a cutting tool at its operative end is passed over the blood vessel section and guide rod assembly. The tube is rotated as it passes over the blood vessel section to sever the connecting branches. After the tube has passed the entire length of the blood vessel section, the section is cut away through the second incision and the tube is removed from the patient with the harvested section inside the tube.

Blood vessel harvesting devices of this type have certain distinct disadvantages. While they eliminate the need for a full length incision to remove the blood vessel segment, two incisions, one at each end of the segment to be harvested, are required in order to remove the blood vessel segment. For patients likely to develop chronic wounds, each additional incision increases the risk to the patient, and it is desirable to keep such incisions as close to the patient's trunk as possible and to minimize the number and size of such incisions. Additionally, such devices are unable to adequately close off several branches of the blood vessel and thus are unable to adequately control bleeding. As a result, the patient suffers greater blood loss than is necessary. These prior devices may also remove more tissue than is necessary because the size of the cutting device is not readily adaptable to the changes in the size of the blood vessel.

In U.S. Pat. No. 5,373,840 to Knighton an improved device and method for vein removal is disclosed which solves some of the problems associated with the use of prior art devices. Knighton discloses an endoscope having a lumen extending longitudinally through the scope body. The endoscope includes means for viewing an area adjacent the distal end of the lumen. The lumen has a lateral dimension large enough to accommodate the blood vessel being harvested and at least one tool for use in harvesting the blood vessel. A first end of the blood vessel section to be harvested is exposed through an incision in the patient's body. A dissecting tool and a gripping tool are inserted through the lumen of the endoscope and used to dissect the blood vessel away from the surrounding connective tissue of the patient's body. Additional tools are provided for use through the lumen of the endoscope to remove body fluids and coagulate bleeding tissue, to ligate and sever side branches from the blood vessel to be harvested, and to ligate and sever a distal end of the blood vessel to be harvested when a desired length of blood vessel has been dissected. Only a small incision in the patient's body is necessary to harvest a relatively long length of blood vessel in a precise and controlled manner using this device and procedure.

Although the '840 patent to Knighton constitutes a significant improvement in devices and techniques for vein harvesting, its multiple tools require more than one operator to complete the procedure. Additionally, its single lumen design requires that the vein be contained within the same lumen as the various tools which are used during the dissection procedure. This makes it possible for the vessel to be damaged during the dissection process by the tools which share the same lumen. It is critical that the segment of blood vessel being harvested is handled with great care since it is destined for reuse (as in arterial bypass). Therefore, it is desirable to isolate the vessel as much as possible from the tools which are used in the dissection.

There is a need for a device and method for vein removal which allows a vein to be harvested in an efficient and safe manner from the body of the patient. Specifically, it would be desirable to provide a device which can be effectively operated by a single operator/physician while at the same time protecting the segment of the vessel being removed from the tools which are used in the procedure.

SUMMARY OF THE INVENTION

In accordance with the present invention there is disclosed a device for removing a generally cylindrical tissue structure from a patient's body. The tissue structure may be a blood vessel, bile duct, tendon or other similar cylindrical/tubular tissue structure which may be removed and/or reused in the patient's body or another patient's body. The device includes an elongated body portion having distal and proximal ends and at least one lumen extending longitudinally therethrough. The lumen is sized to accommodate the tissue structure and at least one tool used in removing the tissue structure. Means is provided for isolating the tissue structure from the tools used in removing the tissue structure in order to protect the tissue structure from damage. The device may include viewing means to enable the operator to remotely view an area adjacent the distal end of the body portion.

The lumen of the body portion may comprise separate vessel and working lumens, the vessel lumen being sized to accommodate the vessel or similar tubular or cylindrical tissue structure and the working lumen or lumens being sized to accommodate the tools used in the removal procedure. The separation of the vessel lumen and working lumens protects the vessel from the tools used in the procedure. Alternatively, the lumen may comprise a single lumen which includes a section which accommodates the vessel and a working section which accommodates the tools.

The vein harvesting device includes means for detachable connection to the vessel. The connection means may comprise an alligator clip like structure which is connected at its proximal end to a tension means which maintains tension on the connection means and hence the vessel in the direction of the proximal end of the body portion when the connection means is connected to the vessel. A housing is provided through which a body portion may be advanced or retracted through the body portion by the operator controlling an advancement means.

The device may include one or more tools sized so that it may be accommodated within the lumen. The tool has a distal operative tip which may be used to cut a side branch of the vessel, cut the vessel, apply a ligation clip to a side branch of the vessel, apply a ligation clip to the vessel, or remove a patient's body fluids.

The device includes means for dissecting the vessel from surrounding tissue. The dissection means may comprise a generally cylindrical structure having a length at least as great as the lumen extending through the body portion. The cylindrical shape defines a lumen which is sized to accommodate the vessel which is drawn into the lumen of the dissection means as the vessel is dissected from surrounding tissue. The dissection means is sized to be accommodated within the vessel lumen. The device includes means for advancing or retracting the dissection means through the lumen.

The invention also includes a method of removing a section of generally cylindrical tissue structure such as a blood vessel from a patient's body. The method includes providing a device having an elongated body portion having distal and proximal ends and at least one lumen extending longitudinally therethrough. The lumen is sized to accommodate the tubular tissue structure and at least one tool used in removing the tissue structure.

A first end of the tubular tissue structure section to be harvested is exposed through an incision in the patient's body. A gripping tool is inserted through the lumen and the first end of the tissue structure is gripped with the tool. The surrounding tissue is dissected away from the tubular tissue structure with a dissecting element. During the procedure the body portion and the dissecting element are advanced along the tubular tissue structure until a desired length of tissue structure is reached such that the dissected portion of the tissue structure extends into the lumen. During the dissection process the tubular tissue structure is isolated from the tools used in removing the tissue structure except at the distal end of the body portion where the dissection procedure is performed. When the desired length of the tissue structure is reached, the tissue structure is cut at its distal end with a transecting tool which may be inserted through the lumen. Alternatively, a second incision can be made through which the distal end of the tissue structure may be cut.

Where the tissue structure being harvested is a blood vessel, the method may further include advancing the body portion and a dissecting element along the vessel until a side branch of the vessel in encountered. A ligation member is then applied to the branch and the branch is cut between the vessel and the ligation member with a ligating-cutting tool inserted through the lumen. The method may also include controlling bleeding as necessary with a bleeding control tool inserted through the second lumen. In one embodiment the method includes providing a viewing element to enable viewing of the vein dissection in progress. In a further embodiment the method includes maintaining tension on the gripping tool in the direction of the proximal end of the body portion such that tension on the vessel is maintained during dissection.

BRIEF DESCRIPTION OF THE DRAWINGS

The foregoing and other aspects of the present invention will be best appreciated with reference of the detailed description of the invention which follows when read in conjunction with the accompanying drawings wherein:

FIG. 1a is a perspective view of the vein removal device of the present invention, FIG. 1b is a fragmented top view of the removable proximal end of the device, and FIG. 1c is a rear view of a portion of the device.

FIGS. 2a and 2b are top views of FIG. 1a illustrating the incremental advancement of the dissecting element and the advancement of the body portion of the device, respectively.

FIGS. 3a, 3b and 3c are partially exploded views of the actuator handle, top view of the actuator lever, and front view of the actuator lever, respectively.

FIGS. 6a and 6b are sectional views taken along line 6—6 of FIG. 1a.

FIGS. 7a and 7b are partial sectional views taken along line 7—7 of FIG. 6a.

FIG. 9b is a top plan view of the distal end of the ligation-cutting tool of FIG. 9a, and FIG. 9c is a side elevational view of the distal end of the ligation-cutting tool of FIG. 9a.

While the above-identified drawing figures set forth one preferred embodiment of the invention, other embodiments are also contemplated, as noted in the discussion. In all cases, this disclosure presents the present invention by way of representation and not by limitation. It should be understood that numerous other modifications and embodiments can be devised by those skilled in the art which fall within the scope and spirit of the principle of this invention. It should be specifically noted that the figures have not been drawn to scale as it has been necessary to enlarge certain portions for clarity. In other figures fragmentary views are shown which omit certain structure for the purpose of more clearly illustrating the invention.

DETAILED DESCRIPTION OF THE INVENTION

The Vein Harvesting Device

Figure 9A:
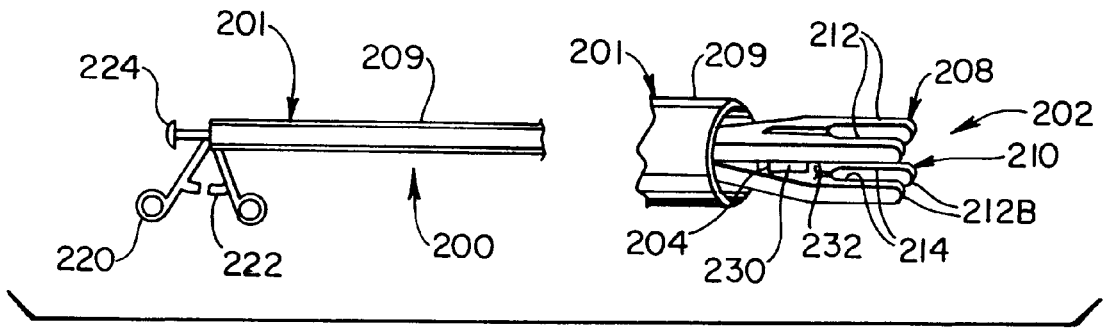
FIG. 9a is a side sectional view of a ligation-cutting tool of the present invention, with its distal end shown enlarged in perspective.
Figure 9B:
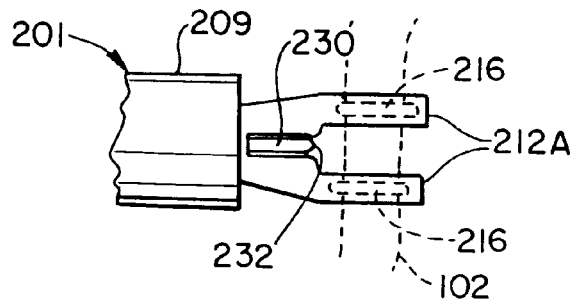
Figure 9C:
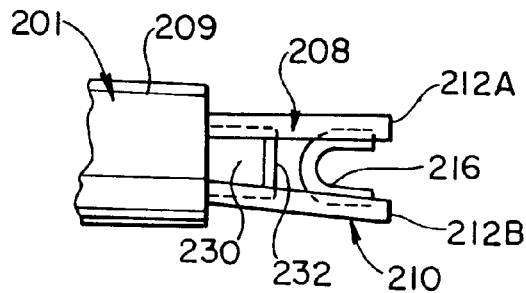
Figure 10:
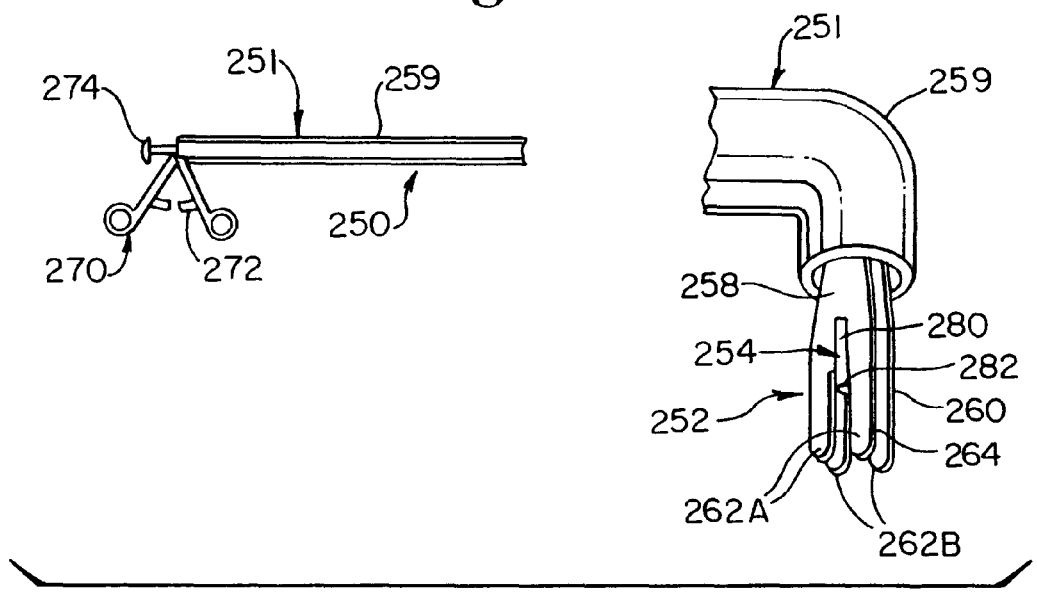
FIG. 10 is a side elevational view of a side-biting ligation-cutting tool of the present invention, with its distal end enlarged in perspective.
Figure 11:
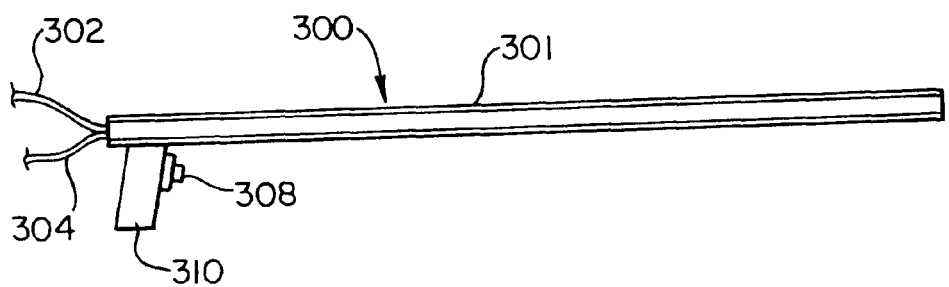
FIG. 11 is a side elevational view of a suction-coagulator tool of the present invention.

The structure of the vein harvesting device of the present invention can be understood generally with reference to FIGS. 1–8. The tools which are used in connection with the device during the vein harvesting procedure are shown in FIGS. 9–11 while FIGS. 12–16 illustrate the device and its associated tools being used in a vein harvesting procedure.

The present invention is a device and method for harvesting a section of cylindrical and/or tubular tissue structure such as a vessel from a patients body. The invention also has application for removing such tissue from animal bodies. The section may be used in another part of a patient's body or for transplanting into a second patient's body. For example, a section of the saphenous vein may be removed for use in coronary bypass surgery. The blood vessel needs to be removed without undue damage to the blood vessel, as well as with minimal damage and trauma to the patient. Although the description herein is directed to the harvesting of the saphenous vein, it is contemplated that the present invention could be used in connection with the efficient and effective harvesting of other vessels, tubular tissue structures or other generally cylindrical structures such as tendons from a patient's body. Structures will generally be comprised of human tissue although the device and methods disclosed herein would work equally well for harvesting synthetic tissue and structures.

FIG. 1a is a perspective view of the vein harvesting device 10 in accordance with the present invention. Device 10 includes a housing 12 through which an elongated body portion 14 is advanced during a vein harvesting procedure. Housing 12 and body portion 14 may be constructed of a rigid material such as metal or plastic. A remote actuation handle 16 is connected to housing 12 by a flexible biaxial cable 18. Actuation handle 16 is used to selectively advance either body portion 14 or vein dissection element 20 in a manner which will be more fully described with respect to FIGS. 2 and 3. Vein dissection element retraction knob 22 protrudes from housing 12 and allows vein dissection element 20 to be retracted during the procedure.

Figure 4:
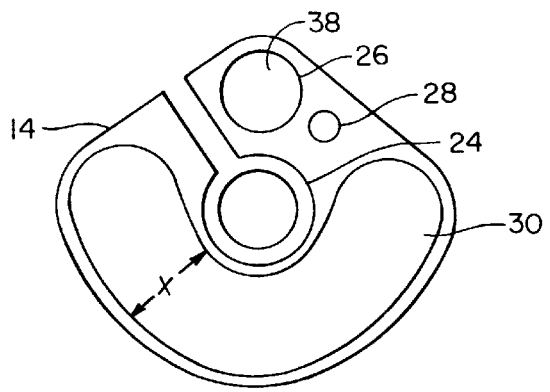
FIG. 4 is a cross-sectional view of a first embodiment of the multi-lumen body portion of the device taken along line 4—4 of FIG. 1.
Figure 8:
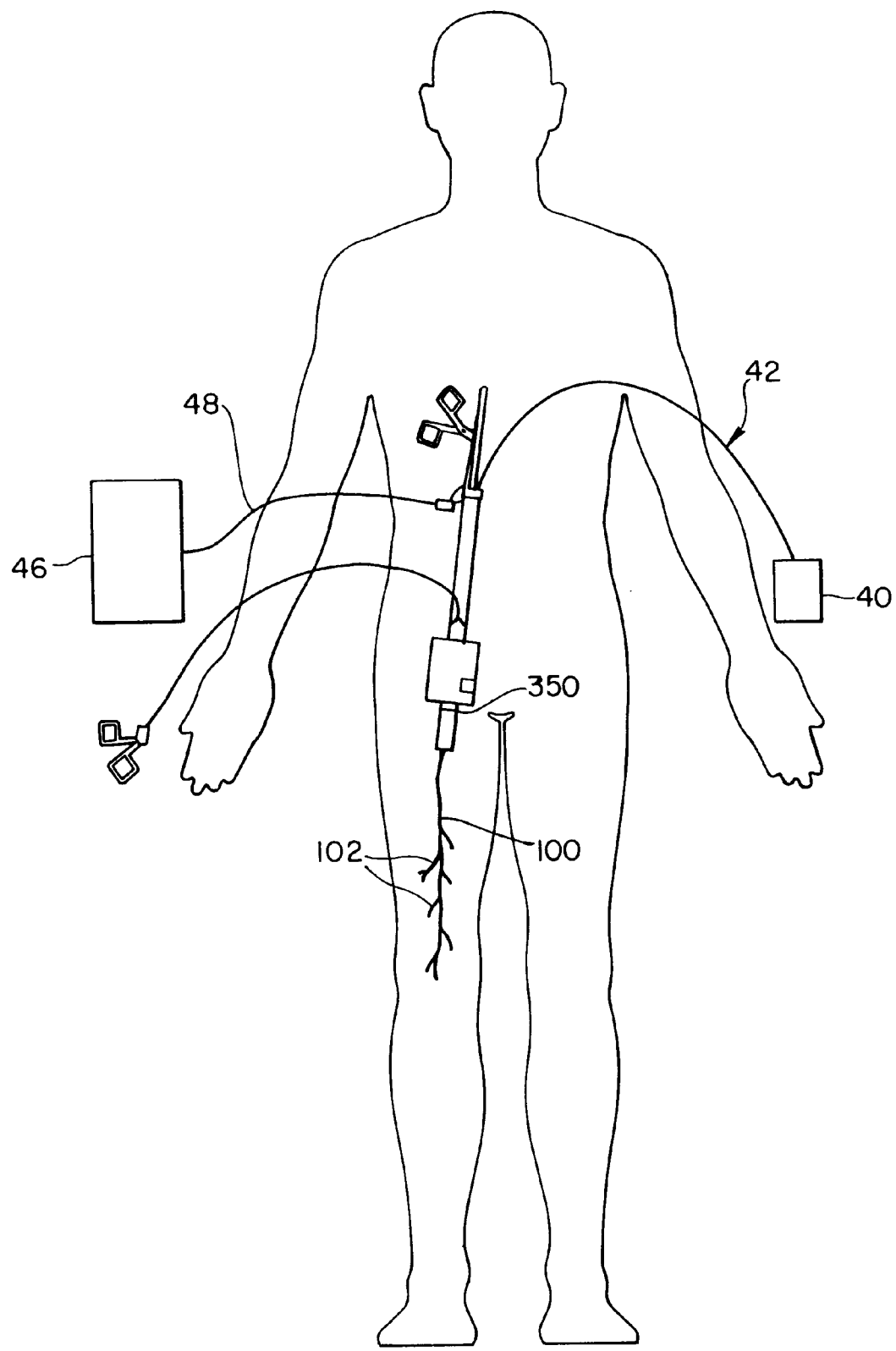
FIG. 8 is a schematic view of the vein harvesting device of the present invention being used in the removal of the saphenous vein of a patient.

As best seen in FIG. 4 which is a sectional view taken along 4—4 in FIG. 1a, body portion 14 includes vessel lumen 24, viewing lumen 26, irrigation lumen 28 and working lumen 30. Each of the lumens runs longitudinally through body portion 14 from an opening at the distal end to an exit port at or near the proximal end of the body portion as seen in FIG. 1c. Working lumen 30 has its exit port 31 at the proximal end of body portion 14. Irrigation lumen 28 has an exit port 29 (FIG. 1a) which may be connected to a source 46 of irrigant (FIG. 8). The function of each lumen will be described in more detail hereafter. Body portion 14 is of sufficient size and shape to accommodate the lumens.

Lumen 24 is of a size large enough to accommodate the blood vessel which is to be harvested and dissection element 20. During the harvesting procedure after an incision has been made and the vein is ligated and clipped, a vein attachment clip 32 is clipped to the vessel. Vein attachment clip 32 is connected via cable 34 to a spring mechanism 36 which maintains a positive tension on the vessel in the direction of the proximal end of the vessel lumen during the dissection procedure. This eliminates the need to use a separate gripping forceps to hold the vessel during the procedure as in U.S. Pat. No. 5,373,840. Vessel lumen 24 may be provided with an irrigation port 25 which may be connected to a source of irrigant (not shown) to allow irrigation of the vessel being harvested, as desired.

Vessel lumen 24 is substantially circular and has a diameter and length which may be varied depending upon the length of the vein section to be harvested and/or the size of the patient from which the vein is to be removed. Typically, the length of body portion 14 will be in the range of 30 to 60 cm and the diameter of the vessel lumen 24 will be in the range of 5–7 mm.

Endoscope lumen 26 is sized to accommodate a fiber optics viewing device 38 which includes an appropriate fiber optics illumination source. Device 38 is positioned such that the area immediately adjacent the distal end of body portion 14 can be illuminated and viewed by the operator. As seen in FIG. 8, device 38 is operably connected to an external monitor 40 which includes a suitable light source by conduit 42. Conduit 42 enters the endoscope lumen at endoscope port 44 (FIG. 1a). Irrigation channel 28 is operable coupled to the external source of irrigant 46 via a suitable conduit 48.

Vein dissection element 20 is used to aid in separating the vessel being harvested from the surrounding tissue. Dissection element 20 has a generally rigid cylindrical body which may be comprised of metal or rigid plastic. The diameter of the cylindrical body of dissection element 20 is sized to accommodate the vessel being harvested. The distal end of the dissection element has a rounded or beveled distal edge 50 used to separate the blood vessel from the surrounding connective tissue as the dissecting element 20 is advanced over the blood vessel. Dissecting element 20 is provided in a plurality of sizes for different sizes of blood vessels. Typical sizes would have inside diameters of 4 mm, 5 mm, and 6 mm. The cylindrical shape of dissection element 20 protects the dissected portion of the vessel which is located within the dissection element. This feature is especially important in those embodiments of the invention where the vessel lumen is not separate from the working lumen (i.e. FIG. 5b).

As an alternative to the cylindrical construction of dissection element 20, the structure may take the form of an elongated shaft having attached at its proximal end an annular dissecting ring. This construction would be similar to the dissecting tool disclosed in U.S. Pat. No. 5,373,840 discussed above. A dissection element so constructed may be inserted through vessel lumen 24 or, in the alternative, may be inserted through a separate working lumen. Utilizing a separate lumen allows the vessel to be completely isolated while in the vessel lumen from the shaft of the dissection element and from all tools used in the procedure.

As seen in FIG. 4, working lumen 30 is generally arcuate in shape and positioned generally around the periphery of vessel lumen 24. Working lumen 30 is sized to accommodate the various tools used in the vein harvesting procedure which will be discussed in more detail with respect to FIGS. 9–11. Typically, lumen 30 will be sized such that dimension X in FIG. 4 is in the range of 5–10 mm. The shape of lumen 30 advantageously allows the tools to be used in various locations around each side and the underside of the vein. Advantageously, the separate working lumen allows the tools used in the procedure to be completely separated from the dissected portion of the vessel in the vessel lumen thus reducing the possibility of damaging the vessel with the tools.

Figure 5A:
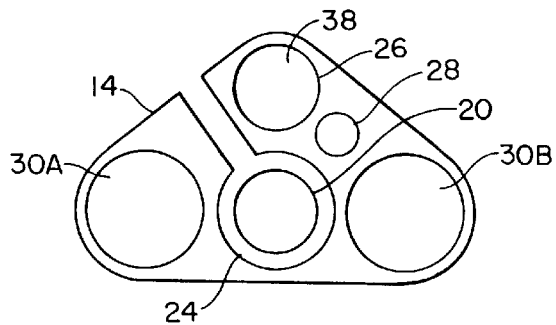
FIG. 5 is a cross-sectional view similar to FIG. 5 of a second embodiment of the body portion of the device of FIG. 1.
Figure 5B:
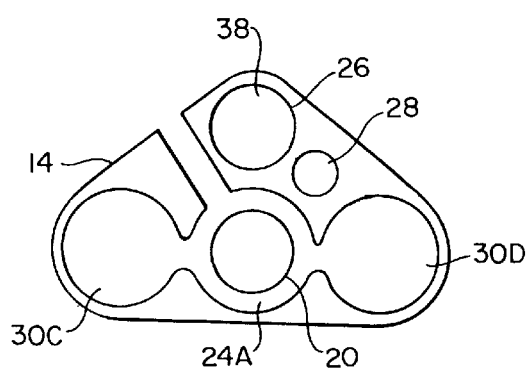

FIGS. 5a and 5b are views similar to FIG. 4 of alternative configurations for body portion 14. Instead of a single arcuate working lumen 30 the body portion is provided with multiple working lumens 30A and 30B in FIG. 5a. In FIG. 5b the working vessel lumens are combined into a single lumen having working sections 30C and 30D and vessel section 24A.

Body portion 14 of FIG. 5a is similar to that of FIG. 4 in that the vessel lumen 24 is separate from the working lumen 30A and 30B. The embodiment of FIG. 5a allows the tools used in harvesting the vein to be inserted on either side of the vessel lumen 24. The size and shape of working lumens 30A and 30B is selected to accommodate the tools used in the procedure. In the embodiment of FIG. 5a the lumens 30A and 30B are generally circular in cross-section and have a diameter in the range of about 5–10 mm.

The embodiment of body portion 14 of FIG. 5b has a single combined working and vessel lumen with working sections 30C and 30D and vessel section 24A. Section 30C and 30D are of a size and shape to accommodate the tools used in the procedure. The vessel is protected from the tools by dissection element 20. Additionally, the vessel may be protected by shaping (i.e. as by narrowing) the junctions between the working sections and the vessel section such that the tools may not substantially enter the vessel section. Other means of protecting the vessel may be employed such as by intermittently partitioning the working sections from the vessel section.

Vein attachment clip 32 is used to hold and retain the vessel being harvested during the procedure. Vein attachment clip 32 includes first and second opposed jaws 52 and 54, respectively. The jaws are tensioned towards the closed position similar to an alligator clip which allows the jaws to obtain a firm grip on the vessel. Alternatively, a latching mechanism may be provided which locks the jaws in a set position. Spring mechanism 36 maintains a positive tension on vein attachment clip 32 through cable 34 towards the proximal end of lumen 24 thus maintaining tension on the vessel during the course of the dissection procedure. Spring mechanism 36 is located within a removable container 37 which is connected to the proximal end of vessel lumen 24 by a bayonet lock mechanism 39. Container 37 may be removed to allow access to the dissected vein by pushing housing 37 towards the distal end of body portion 14 while twisting the housing 90° clockwise.

Figure 6A:
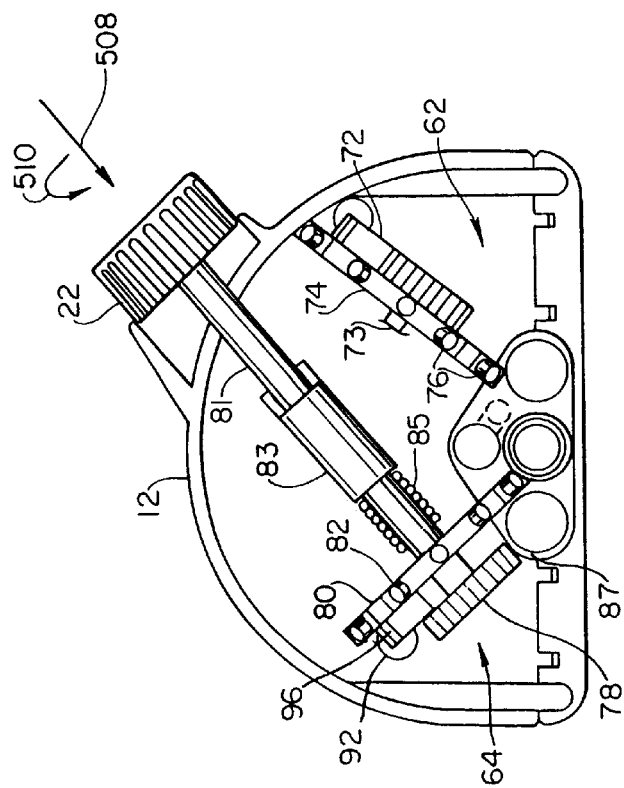
Figure 6B:
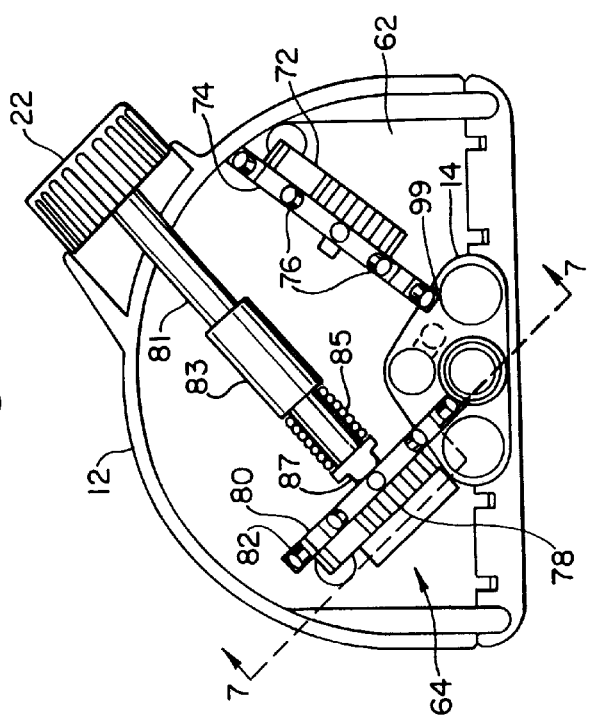

As best seen in FIGS. 3a, 3b and 3c remote actuation handle 16 is a scissors-type actuator and includes a lever 56. Lever 56 is positioned so that it may be moved to the right or left by the thumb of the operator. Lever 56 is used to engage one of two cables, 58 and 60, one of which is connected through biaxial cable 18 to a body portion advancement mechanism 62 and the other of which is connected to a dissection element advancement mechanism 64 (FIGS. 6a and 6b). For example, the operator may choose to advance body portion 14 by moving lever 56 to the left. Lever 56 includes notches 66A and 66B which accommodate cables 58 and 60, respectively. When lever 56 is moved to the left as shown in FIG. 3c cable 58 fits within notch 66A. A stop 68 is provided at the end of cable 58 which is larger than notch 66A so that when the operator squeezes the handles of the scissors-type actuating handle together cable 58 is retracted from biaxial cable 18. Similarly, a stopped 70 is provided on cable 60 so that when lever 56 is moved to the right cable 60 may be retracted by squeezing scissors-type actuation handle 16. Thus, by moving lever 56 to the left or the right the operator can select whether to advance body portion 14 or dissection element 20.

The details of the body portion advancement mechanism 62 and dissection element mechanism 64 are shown in FIGS. 6a, 6b, 7a and 7b. FIGS. 6a and 6b are cross-sectional views of the interior of the housing 12. Body portion advancement mechanism 62 includes ratchet wheel 72 fixedly connected to a spoked wheel 74 which rotates about an axle 73. Axle 73 is fixedly mounted to housing 12 in a manner not shown in FIGS. 6a and 6b in order to simplify the Figures for purposes of clarity. Wheel 74 has spaced along its circumference a plurality of generally circular pegs 76. Similarly, dissection element advancement mechanism 64 includes a toothed ratchet wheel 78 fixedly connected to a spoked wheel 80 having a plurality of pegs 82 spaced along its circumference. In a manner which will be described in more detail with respect to FIGS. 7a and 7b, retraction by the operator of cable 58 actuates body portion advancement mechanism 62 causing body portion 14 to advance in the distal direction through housing 12 while retraction of cable 60 causes dissection element advancement mechanism 64 to advance dissection element 20 through lumen 24.

Figure 7B:
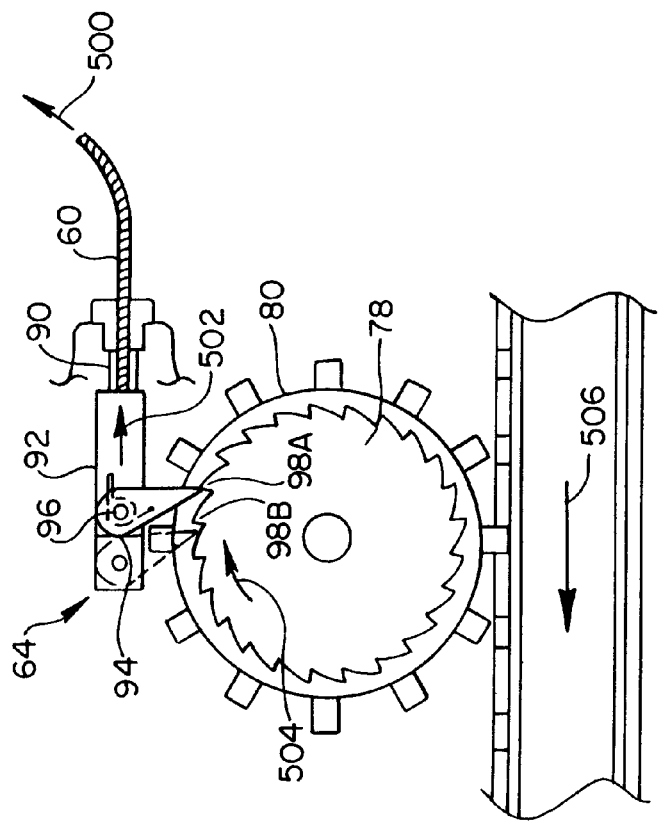
Figure 7A:
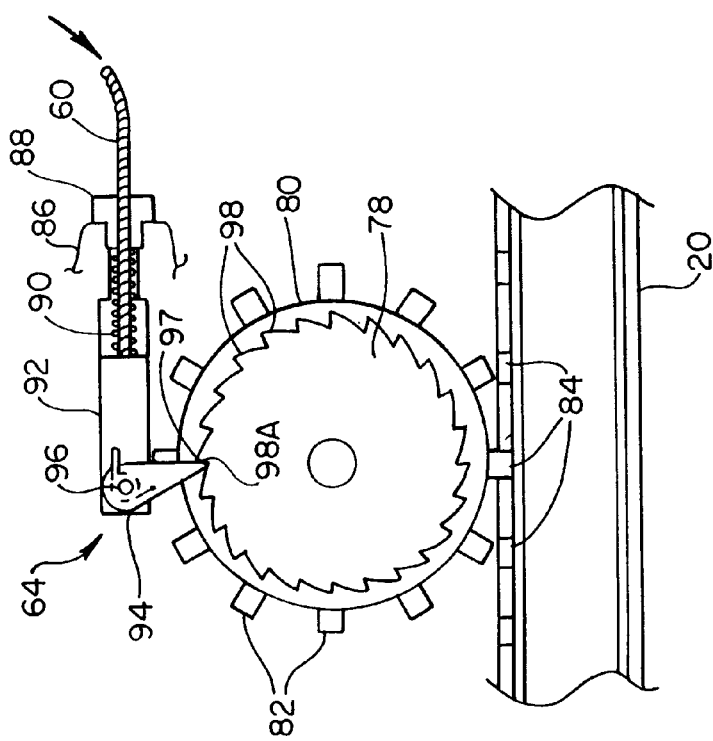

FIGS. 7a and 7b are fragmentary cross-sectional views of dissection element advancement mechanism 64 showing cable 60 in the extended position (FIG. 7a) and in the retracted position (FIG. 7b). Spokes 82 along the circumference of spoked wheel 80 extend through a slot 86 in body portion 14 (FIGS. 4 and 5) and align with mating openings 84 on the surface of dissection element 20. Therefore, rotation of spoked wheel 80 causes either advancement or retraction of dissection element 20 depending upon direction of rotation. Rotation of spoked wheel 80 may be imparted by retraction of cable 60 by the operator manipulating remote actuator 16 in the appropriate manner. If lever 56 is moved to the right to engage cable 60 actuation of the scissors-type actuator handle 16 will cause a retraction of cable 60. Cable 60 extends through biaxial cable 18 into housing 12 through a fixed member 86 which is either a portion of the housing or fixed thereto. Fixed member 86 has a plug 88 which acts as a stop for a spring 90. Cable 60 extends through plug 88 and spring 90 and is fixedly connected to a movable cylinder 92 ratchet arm 94 is movably connected to one side of cylinder 92. A Ratchet arm 94 pivots about a point 96 and is positioned such that its narrow distal tip 97 mates with teeth 98 on toothed ratchet wheel 78.

When cable 60 is in the extended position as shown in FIG. 7a the distal tip 97 of ratchet arm 94 engages one of the teeth 98A on toothed wheel 78. When cable 60 is retracted by the operator, cable 60 moves towards the operator in the manner shown in FIG. 7b. Retraction of cable 60 in the direction of arrow 500 causes cylinder 92 to move in the direction of arrow 502. Ratchet arm 94 which is engaged by tooth 98A and causes both toothed wheel 78 and spoked wheel 80 to rotate in the direction of arrow 504. One squeeze of remote actuator handle 16 causes spoked wheel 80 to rotate an amount corresponding to the distance between teeth on toothed wheel 78. Preferably, each squeeze of the actuation handle will cause the dissection element to advance 5 mm. This is a significant feature of the present invention since it allows the operator to precisely and accurately control the advancement of the dissection element (or the body portion) in discreet incremental steps. When the remote actuator handle 16 is released cylinder 92 returns to its original position (shown in dotted line in FIG. 7b) due to the force exerted by spring 90. Pivot arm 96 is constructed so that it is fixed with respect to rotation towards the left side of FIG. 7b but will rotate towards the right side of FIG. 7b. Thus, when cylinder 92 moves to the position it occupied in FIG. 7a as shown in dotted line in FIG. 7b, pivot arm 96 will ride over the surface of the next tooth 98B. It thus returns to the position of FIG. 7a and is ready for the next incremental advancement of dissection element 20.

Body portion 14 is advanced in a manner similar to that of dissection element 20. The only difference being that pegs 76 of spoked wheel 74 are aligned to engage with mating openings 99 in body portion 14. Lever 56 is moved to the right so that activation of scissors-type handle 16 will cause incremental advancement of body portion 14.

As best seen in FIGS. 6a and 6b retraction knob 22 is provided to enable dissection element 20 to be retracted by the operator during the vein harvesting procedure. In the preferred embodiment vein dissection element 20 is advanced in 5 mm increments to a length of about 5 cm past the distal end of the body portion as shown in FIG. 2a. Once the dissection element 20 has been extended a desired distance beyond the distal end of body portion 14, body portion 14 is advanced as shown in FIG. 2b. As seen in FIGS. 6a and 6b a suitable clutch 87 is provided to prevent dissection element 20 from being advanced when a side branch is encountered. Clutch 87 may be of conventional construction and function to cause toothed ratchet wheel 78 to slip with respect to spoked wheel 80 if the resistance in the advancement of dissection element 20 exceeds a predetermined level which may cause damage to the side branch. When a side branch is encountered or when the desired length of vessel has been obtained dissection element 20 may be retracted.

Retraction of dissection element 20 is accomplished as shown in FIG. 6b by depressing retraction knob 22 in the direction of housing 12. Knob 22 is connected to shaft 81 which extends through a stationary guide 83. Knob 22 and shaft 81 are biased in the position shown in FIG. 6a by a spring 85. When knob 22 is depressed as in the direction of arrow 508 in FIG. 6b shaft 81 causes toothed ratchet wheel 78 to become disengaged from pivot arm 96. Thus rotation of knob 22 in a counterclockwise direction as shown by arrow 510 causes spoked wheel 80 to rotate in a direction opposite to that shown by arrow 505 in FIG. 7b. This correspondingly causes dissection element 20 to move in a direction opposite arrow 506 thus resulting in retraction of dissection element 20.

The Tools

As shown in FIG. 8 when device 10 is used to harvest a blood vessel such as a saphenous vein 100, the device is used in conjunction with several tools. These tools are inserted into the working lumen 30 (FIG. 4), 30A, 30B (FIG. 5a), or sections 30C, 30D (FIG. 5b) of body portion 14 at an entrance port (i.e. port 31, FIG. 1c) located at the proximal end of the lumen. This allows the tools to be isolated from the vein during the dissection procedure to further protect the vein from any damage from tools being inserted, retracted or manipulated during the course of the procedure. A ligation-cutting tool 200 (FIG. 9) is used when severing side branches 102 from the blood vessel 100. A side-biting ligation-cutting tool 250 (FIG. 10) is used to transect the blood vessel 100 when the dissection is completed. Finally, a suction-coagulator tool 300 (FIG. 11) is used to control bleeding during the procedure.

The ligation-cutting tool 200 (FIG. 9a, 9b and 9c) is used to sever and seal side branches on the vessel being harvested. The ligation-cutting tool 200 has an elongated shaft 201, with a ligation clip applicator 202 and a cutting mechanism 204 at the distal end of the shaft 201. The ligation clip applicator 202 includes a first yoke 208 and a second opposed yoke 210. Each yoke 208 and 210 is in turn divided into two sections. Each yoke 208 and 210 is forked at its distal end, forming two opposed prongs 212A and 212B on the yokes 208 and 210, respectively. The prongs 212A and 212B on the yokes 208 and 210 are parallel to each other and generally aligned with the longitudinal axis of the ligation-cutting tool 200. The yokes 208 and 210 and the prongs 212A and 212B thereon oppose each other and serve to apply ligation clips 216 (see FIGS. 9b and 9c) to a side branch 102 being severed. The opposing prongs 212A and 212B of each yoke 208 and 210 contain two grooves 214 respectively, to securely hold a ligation clip 216 therein. When the ligation clips 216 are thus held between the opposing prongs 212A and 212B of yokes 208 and 210, the generally U-shaped ligation clips 216 aid the operator in properly aligning the ligation-cutting tool 200 and the side branch 102 to be ligated by providing an abutment for the side branch 102 when side branch 102 is positioned between yokes 208 and 210. When the yokes 208 and 210 are biased towards each other in a conventional manner, the ligation clips 216 are deformed to clamp onto the side branch 102 there between and the blood flow through the side branch 102 is halted at two slightly spaced apart points (e.g., two clips are applied approximately 0.25 inches apart). When the ligation clip applicator 202 is activated and the yokes 208 and 210 clamp the ligation clips 216 onto the side branch 102, the side branch 102 is held securely for cutting the side branch 102.

The cutting mechanism 204 on the ligation-cutting tool 200 includes a cutting blade 230 aligned between the prongs 212A and 212B and proximal to the ligation clips 216. The cutting blade 230 is normally retracted (as seen in FIGS. 9a, 9b and 9c) to allow the side branch 102 to be positioned properly between the yokes 208 and 210. A cutting edge 232 of the blade 230 faces the distal end of the ligation-cutting tool 200 and the cutting motion of the blade 230 is in a distal direction (e.g., towards the side branch 102). The blade 230 is wide enough to completely sever the side branch 102 between the two yokes 208 and 210. The cutting mechanism 204 is activated by the operator (as described below) after the side branch 102 has been ligated (i.e., the side branch 102 has been clipped shut and blood flow halted) and while the side branch is still held securely in the yokes 208 and 210. After the blade 230 has severed the side branch 102, the blade 230 returns into its original retracted position.

The ligation clip applicator 202 and the cutting mechanism 204 are both actuated by mechanisms by the proximal end of the shaft 201 of the ligation-cutting tool 200. The ligation clip applicator 202 is preferably actuated by a scissors-type handle 220. By squeezing the scissors-type handle 220, the operator causes each set of prongs 212A and 212B on the yokes 208 and 210 to be moved together, thereby compressing their respective ligation clip 216 about the side branch 102 of the blood vessel 100 as described above. The scissors-type handle 220 includes a latching mechanism 222 which serves to secure the handle 220 and thus the ligation clip applicator 202 in a closed or clamped position. While the ligation clip applicator 202 is held in a clamped position, the cutting mechanism 204 is actuated, preferably by a plunger 204 located at the proximal end of the ligation-cutting tool 200. The plunger 224 is operably connected to the cutting blade 230 and biased proximally to urge the blade 230 into its normally retracted position. By moving the plunger 224 distally, the operator causes the cutting blade 230 to likewise move distally and cut the side branch 102 of the blood vessel 100 which is retained between the yokes 208 and 210. When the operator releases the plunger 224, the plunger 224 (and thus the cutting blade 230) retracts to its original position. Manipulation of the handle 220 then separates the prongs 212A and 212B, leaving the clip in place on the severed portions of the side branch 102 and the ligation-cutting tool 200 is removed or relocated for reuse (the clips may be fed into place in the grooves of the prongs from a suitable clip magazine not shown) to enable multiple ligations without removing the tool from the body.

The shaft 201 of the ligating-cutting tool 200 is a slender member that is longer than the working lumen (30 in FIG. 4, 30A, 30B in FIG. 5a, 30C, 30D in FIG. 5b). A housing 209 covers those mechanisms on the shaft 201 that transmit the manipulations of the handle 220 and the plunger 224 at the proximal end of the ligation-cutting tool 200 to the clipping and cutting motions, respectively, at the distal end of ligation-cutting tool 200.

The side biting-ligation-cutting tool 250 (FIG. 10) is used to sever and seal the distal end of the vessel being harvested. The side-biting ligation-cutting tool 250 is identical in operation to the ligation tool 200, except that the operative components at the distal end of the tool 250 are oriented generally normally to the axis of the tool 250. As seen in FIG. 10, the side-biting ligation-cutting tool has an elongated shaft 251, with a ligation clip applicator 252 and a cutting mechanism 254 at the distal end of shaft 251. The ligation clip applicator 252 includes a first yoke 258 and a second, opposed yoke, 260. Each yoke in turn is forked at its distal end, forming two opposed prongs 262A and 262B, respectively. The prongs are aligned generally parallel and each has two grooves 264 to retain ligation clips between each opposed pair of prongs 262A and 262B. The structure and operation of the ligation clip applicator 252 is similar to that illustrated in FIGS. 9b and 9c for the ligation-cutting tool 200.

The yokes 258 and 260 and the prongs 262A and 262B thereon oppose each other and serve to apply ligation clips not shown in FIG. 10 to the distal end of the segment of the blood vessel being severed. When the ligation clips are thus held between the opposing prongs 262A and 262B of yokes 258 and 260, the generally U-shaped ligation clips aid in positioning and properly aligning the side-biting ligation-cutting tool 250 and the blood vessel to be transected by providing an abutment for the blood vessel when the blood vessel is positioned in the yokes 258 and 260. When the yokes 258 and 260 are moved towards each other, the ligation clips are clamped onto the blood vessel there between and the blood flow through the blood vessel is halted at two slightly spaced-apart points (e.g., two clips are applied approximately 0.25 inches apart). When the ligation clip applicator 252 is activated and the yokes 258 and 260 clamp the ligation clips onto the blood vessel, the blood vessel is also held securely for cutting the blood vessel.

The cutting mechanism 254 on the side-biting ligation-cutting tool 250 includes a cutting blade 280 aligned between the prongs 262A and 262B. Again, the structure of the cutting mechanism for the tool 250 is quite similar to that illustrated in FIGS. 9b and 9c for the ligation-cutting tool 200. The blade 280 is positioned such that a cutting edge 282 of the blade 280 does not interfere with the alignment of the blood vessel between the yokes 258 and 260. The cutting blade 280 is normally retracted (as seen in FIG. 10) to allow the blood vessel to be positioned properly between yoke 258 and 260. The cutting edge 282 of the blade 280 faces in a transverse direction from the shaft 251 of the side-biting ligation-cutting tool 250, and the cutting motion of the blade 280 is in a transverse direction (e.g., toward the blood vessel). The blade 280 is wide enough to completely sever the blood vessel between the two yokes 258 and 260. The cutting mechanism 254 is activated after the blood vessel has been ligated (the blood vessel has been clipped shut and the blood flow halted) and while the blood vessel is still held securely in the yokes 258 and 260. After the blade 280 has severed the blood vessel, the blade 280 returns to its original retracted position.

The primary difference between the tool 200 and tool 250 is that the distal operative portion of the tool 250 is oriented at an angle generally 90 degrees opposed to the axis of the shaft 251 of the tool 250. The yokes 258 and 260 are thus oriented to straddle a blood vessel extending generally parallel to the shaft 251 to apply ligation clips thereto. After clips are applied, the yokes continue to hold the blood vessel to permit severing of the vessel using the blade 280. Other than the revision in orientation of the distal portion of the ligation-cutting tool 250, it operates in the same manner as the ligation-cutting tool 200.

The ligation clip applicator 252 and the cutting mechanism 254 are both actuated by mechanisms at the proximal end of the shaft 251 of the ligation-cutting tool 250. The ligation clip applicator 252 is preferably actuated by a scissors-type handle 270. Squeezing of the scissors-type handle 270 causes each pair of prongs 262A and 262B -on the yokes 258 and 260 to move together, thereby compressing their respective ligation clips about the blood vessel. The scissors-type handle 270 includes a latching mechanism 272 which serves to secure the handle 270 and thus the ligation clip applicator 252 in a closed or clamped position. While the ligation clip applicator is held in a clamped position, the ligation cutting mechanism 254 is actuated, preferably by a plunger 274 located at the proximal end of the ligation-cutting tool 250. The plunger 274 is operably connected to the cutting blade 280, and biased proximally to urge the blade 280 into its normally retracted position. By moving the plunger 274 distally, the operator causes the cutting blade 280 to likewise move distally and cut the blood vessel which is retained between the yokes 258 and 260. When the operator releases the plunger 274, the plunger 274 (and thus the cutting blade 280) retracts to its original position. Manipulation of the handle 270 then separates the prongs 262A and 262B, leaving the clips in place on the severed portion of the blood vessel, and the ligation-cutting tool 250 is removed.

The shaft 251 of the side-biting ligation-cutting tool 250 is a slender member that is longer than the working lumen of device 10. A housing 259 covers those mechanisms on the shaft 251 that transmit the manipulations of the handle 270 and the plunger 274 at the proximal end of the side-biting ligation-cutting tool 250 to the clipping and cutting motion, respectively, at the distal end of the side-biting ligation-cutting tool 250.

The suction-coagulator tool 300 (FIG. 11) is used to remove body fluid (e.g., blood) and reduce bleeding during the vessel harvesting procedure, and is of the type generally known in the art for this procedure. The suction-coagulator tool 300 has an elongated shaft 301 and includes a handle 310 attached to the proximal end of the shaft 301. A suction tube 302 is attached to the proximal end of shaft 301 and extends to the distal end of shaft 301. At the distal end of shaft 301 the suction tube 302 is opened for suctioning body fluids. Also attached to the proximal end of shaft 301 is a power cable 304 for supplying power for tissue coagulation. When button 308 on handle 310 is activated, the power is supplied to the distal end of shaft 301 to cauterize bleeding tissue, and thus to stop bleeding. The suction-coagulator tool 300 controls bleeding in two ways. The suction tube 302 may be used alone to suction any body fluids from the dissection area, or the coagulator may be used to cauterize the bleeding tissue.

Method of Operation

Figure 12:
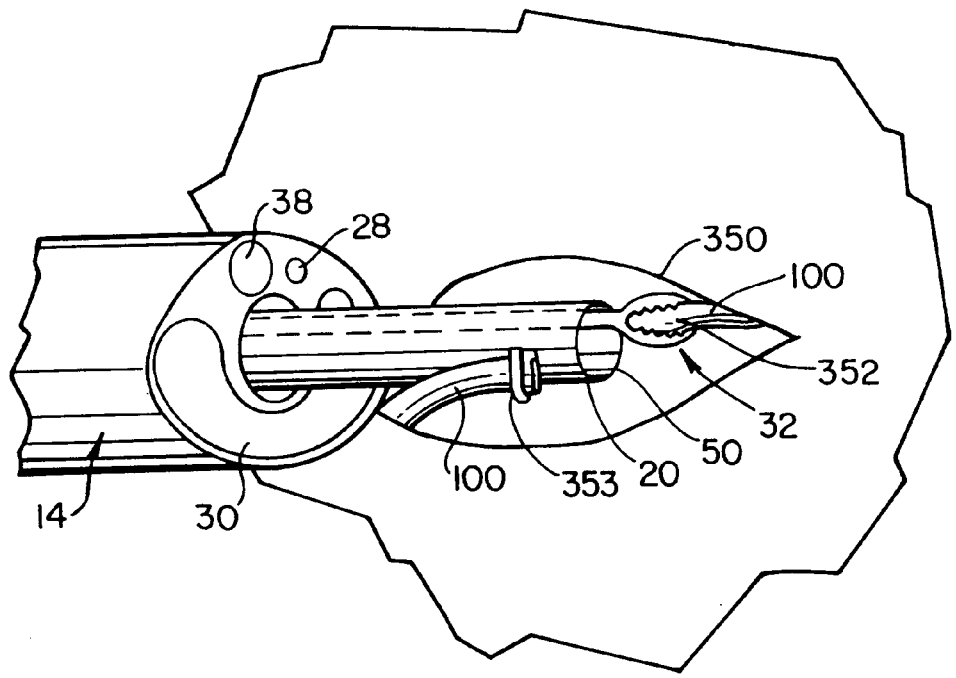
FIGS. 12 and 13 are enlarged perspective illustrations showing the distal end of the vein harvesting tool in use during the harvesting of a blood vessel.

The vein harvesting device 10 and accompanying tools 200, 250 and 300 are used in combination for harvesting a vessel. After proper preparation of the incision site, the physician makes a small incision 350 (e.g. 3 cm long) over the proximal aspect of the blood vessel to be harvested (see FIGS. 8 and 12). The blood vessel 100 is exposed and dissected for a short length under direct vision. As seen in FIG. 12, the blood vessel 100 is then severed to expose a free end 352 and a free end 353 (which may be clipped as shown in FIG. 12). For example, to remove a saphenous vein, the incision 350 will be made at the groin over the saphenous vein and the vein will be dissected free from the junction common femoral vein. As shown in FIGS. 8 and 12, the vein attachment clip 32 is inserted through the dissecting element 20, both of which are accommodated within vessel lumen 24 of vein harvesting device 10 such that the distal ends of dissecting element 20 and vein attachment clip 32 extend beyond the distal end of lumen 24. The free end 352 of blood vessel 100 is attached to vein attachment clip 32 such that it is held under tension in the manner previously described. The vein harvesting device 10 is secured in a fixed position to the patient's body such as with tape. The dissecting element 20 is then advanced distally over the distal end of the attachment clip 32 and over the blood vessel 100. As the dissecting element 20 is manipulated by the operator from remote actuation handle 16, the blood vessel 100 is dissected away from surrounding connective tissue.

Figure 13:
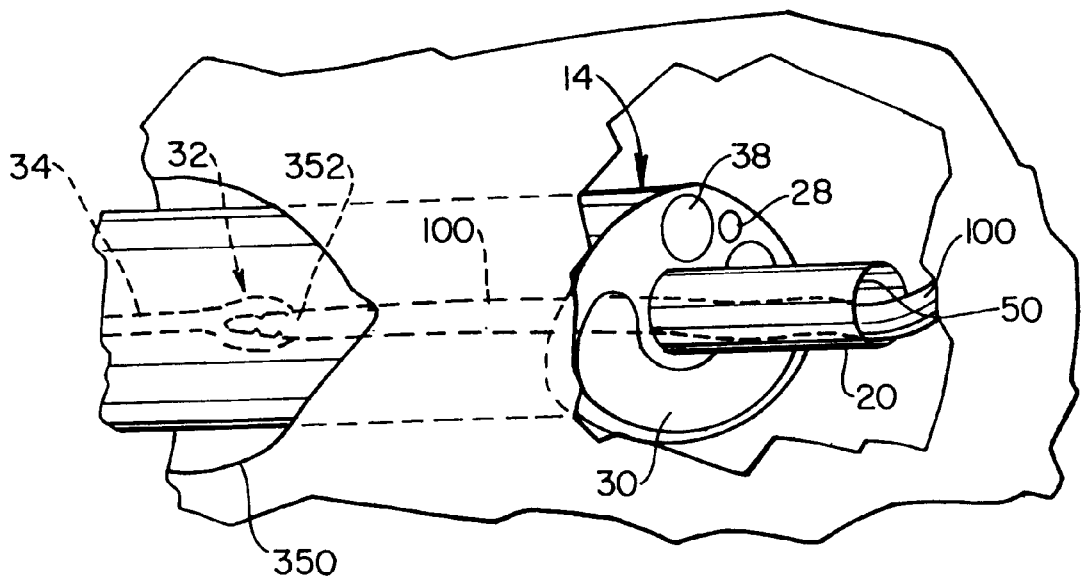
Figure 14:
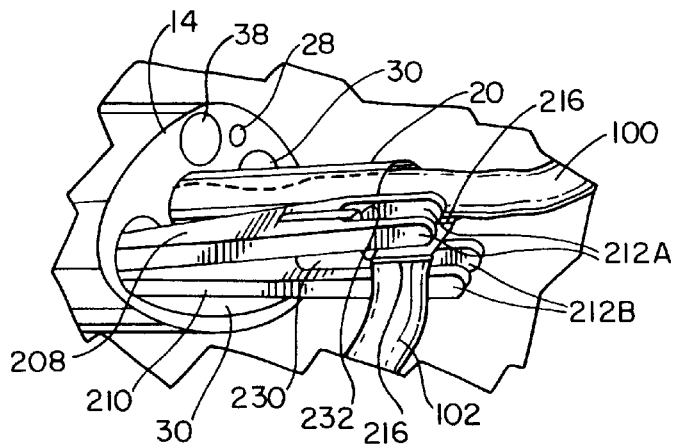
FIGS. 14, 15 and 16 are enlarged perspective illustrations showing the distal end of the vein harvesting device and the tools of FIGS. 9–11 in use during the harvesting of a blood vessel.

As illustrated in FIG. 13 (which has a portion of the patient's body broken away to show the invention in operation), the dissection process proceeds distally along the blood vessel 100. The body portion 14 is advanced along with the dissecting element 20 into the incision 350. Until this point, the operator has been viewing the procedure under direct vision. Now, the operator switches to viewing the dissection process (occurring at the area immediately adjacent the distal end of the lumen 24) through the fiber optic viewing device 38 located at the distal end body portion 14. Alternatively, the vein device could be provided by a separate scope. As previously discussed, device 38 provides adequate lighting for the operator to view the dissection and tool operations occurring within the patient via the monitor. Irrigant is introduced as necessary through irrigation channel 28 to keep blood or other body tissue from obscuring vision adjacent the distal end of the body portion 14.

As the dissection element 20 is advanced along the blood vessel 100, a side branch 102 of the blood vessel 100 may be encountered before the desired length of blood vessel 100 has been dissected. As previously discussed, clutch 87 (FIGS. 6a and 6b) prevents dissection element from being advanced when a side branch is encountered. This is particularly important when the side branch lies under vessel 100 where it may not be visible to the operator. When a side branch is encountered before obtaining the desired length of blood vessel, the ligation-cutting tool 200 is employed to sever the side branch 102 from the vessel 100 being harvested as shown generally in FIGS. 14 and 15. When a side branch 102 is reached, the operator stops advancing the dissecting element 20 and the body portion 14 and, if necessary, withdraws the dissecting element 20 proximally from the side branch 102 to provide room for the operation of the ligation-cutting tool 200. The ligation-cutting tool 200 is inserted into the proximal end of working lumen 30 and advanced distally through lumen 30 and into the area distal of body portion 14. The operator positions the ligation-cutting tool over the side branch 102 such that the side branch 102 is sitting in the yokes 208 and 210 (see FIG. 14). The operator then manipulates the handle 220 of the ligation-cutting tool 200 to actuate the ligation clip applicator 202. As the prongs 212A and 212B on each of the yokes 208 and 210 move toward each other, the ligation clips 216 are clamped about the side branch 102 thereby stopping blood flow to the side branch 102.

Figure 15:
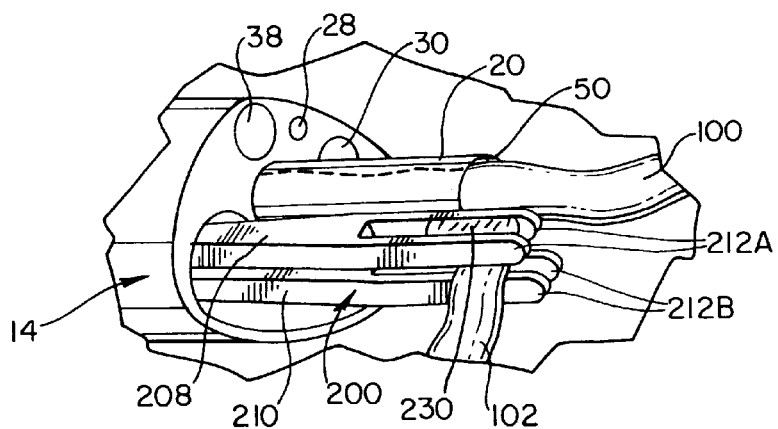

While the side branch 102 is held securely between the yokes 208 and 210 of the ligation clip applicator 202, the operator pushes the plunger 224 to activate the cutting mechanism 204. As shown in FIG. 15, the cutting blade 230 thus moves distally into and through the side branch 102, thereby severing the side branch 102 from the blood vessel 100 between the ligation clips 216. When the plunger 224 is released by the operator, the cutting blade 230 returns to its original retracted position. The handle 220 is then manipulated to separate the prongs 212A and 212B, and the ligation-cutting tool 200 is withdrawn proximally through the working lumen 30 of body portion 14. The ligation-cutting tool 200 may then be prepared to be used again later in the procedure (i.e., reloaded with additional clips 216), if required.

After the ligation-cutting tool 200 has been removed from the working lumen 230, the dissecting element 20 and body portion 14 are again advanced distally along the blood vessel 100 by the operator using the remote actuation handle 16 (as previously described) until another side branch is reached. In this regard, the dissecting element 20 is large enough to pass over the clip and severed stumps of any side branches 102 which extend from the blood vessel 100. The ligation-cutting tool 200 is then used as previously described to sever additional side branches from the blood vessel 100. The procedure is repeated until the desired length of blood vessel 100 has been dissected free from all the surrounding tissue and side branches.

During the dissection procedure, the suction-coagulator tool 300 is used as required to control bleeding, again under the constant vigilance of the operator. During the entire procedure, the blood vessel 100 has been held in tension by vein attachment clip 32 which is biased in the proximal direction by spring mechanism 36. It is, thus, unnecessary for the operator to use a separate gripping tool for the purpose of holding the vessel under tension. This frees the operator to concentrate on the other aspects of the dissection procedure. As more and more of the blood vessel 100 becomes dissected, the body portion 14 is advanced distally into the patient's body and the blood vessel 100 is moved into vessel lumen 24 of body portion 14.

Figure 16:
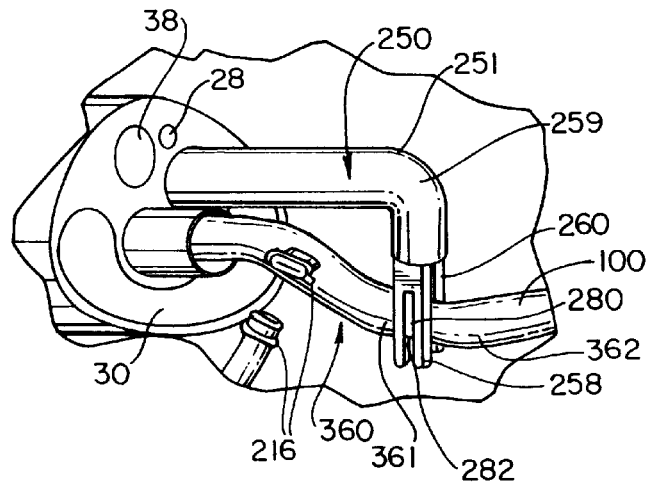

When the desired length of blood vessel 100 has been dissected free from the surrounding connective tissue, the dissecting element 20 is moved proximally away from the distal end of the dissected vessel segment, and the side-biting ligation-cutting tool 250 is inserted into the proximal end of the working lumen 30 and advanced distally through lumen 30 into the area adjacent the distal end of body portion 14 and the distal end of the dissected blood vessel 100. The side-biting ligation-cutting tool 250 is positioned such that the blood vessel 100 is between the first yoke 258 and the second yoke 260 of the ligation clip applicator 252, as seen in FIG. 16. When the blood vessel 100 is properly positioned between yokes 258 and 260, the operator manipulates the handle 270 to actuate the ligation clip applicator 252. As the yokes 258 and 260 move toward each other, the yokes 258 and 260 act to pinch the ligation clips 266 over the distal end of the dissected blood vessel 100 (thus stopping blood flow through the blood vessel 100). While the blood vessel 100 is held securely by the ligation clip applicator 252, the operator pushes the plunger 274 to activate the cutting mechanism 254. The cutting blade 280 advances between the ligation clips 266 and through the blood vessel 100 to sever the blood vessel 100 into a freed section 360 having free end 352 (FIG. 12) and a free end 361 (FIG. 16) and a remaining section 362. When the plunger 274 is released by the operator, the cutting blade 280 returns to its retracted position. The handle 270 is manipulated to separate the prongs 262A and 262B, and the side-biting ligation-cutting tool 250 is withdrawn proximally through the lumen 30 of body portion 14. The tool 250 may apply ligation clips on sections 360 and 362, or just one clip on the remaining section 362 of the blood vessel 100.

The freed section 360 of the blood vessel 100 is now free of all connections to the patient's body and is substantially within vessel lumen 24 of body portion 14. The desired section of dissected vessel may be removed by releasing the bayonet lock 39 at the proximal end of vessel lumen 24 and then by pulling the vein through the proximal end of lumen 24. Once removed the freed section 360 of blood vessel 100 may then be prepared for its intended use or be discarded.

What is claimed is:

1. A system for removing a generally cylindrical tissue structure from a human or animal body, comprising:

a tool having a distal operative tip for performing at least one of cutting a side branch of the tissue structure, cutting the tissue structure, applying a ligation clip to a side branch of the tissue structure, applying a ligation clip to the tissue structure and removing body fluids;

an elongated body portion having a distal end and a proximal end, the body portion having at least one lumen extending longitudinally therethrough, the at least one lumen being sized to accommodate the tissue structure and the tool used in removing the tissue structure; and a generally cylindrical tissue structure dissection element sized to fit within the at least one lumen, the dissection element having a lumen sized to accommodate the tissue structure and to isolate the tissue structure from the tool along a substantial portion of the at least one lumen of the body portion.

2. The system of claim 1 further comprising means for viewing an area adjacent the distal end of the body portion.

3. The system of claim 1 further including a tissue attachment member adapted for detachable connection to the tissue structure, the attachment member being sized to fit within the lumen of the dissection element.

4. The system of claim 3 further comprising a tension element having a distal end connected to the attachment member for maintaining tension on the tissue structure in the direction of the proximal end of the body portion when the attachment member is connected to the tissue structure.

5. The system of claim 1 further including a housing through which the elongated body portion is advanced or retracted.

6. The system of claim 5 further including a body portion advancement member operably connected to the body portion for advancing or retracting the body portion through the housing.

7. The system of claim 1 further comprising a dissection element advancement member operably connected to the dissection element for advancing or retracting the dissection element through the at least one lumen.

8. The system of claim 7 further comprising a clutch element to prevent advancement of the dissection element if a predetermined amount of resistance is encountered.

9. A system for removing a generally cylindrical tissue structure from a human or animal body comprising:

a tool having a distal operative tip for performing at least one of cutting a side branch of the tissue structure, cutting the tissue structure, applying a ligation clip to a side branch of the tissue structure, applying a ligation clip to the tissue structure and removing body fluids;

an elongated body portion having a distal end and a proximal end, the body portion having at least one lumen extending longitudinally therethrough, the at least one lumen being sized to accommodate the tissue structure and the tool used in removing the tissue structure; and means for isolating the tissue structure from the tool used in removing the tissue structure.

10. The system of claim 9 further comprising means for viewing an area adjacent the distal end of the body portion.

11. The system of claim 9 wherein the at least one lumen includes first and second lumens, the first lumen being sized to accommodate the tissue structure and the second lumen being sized to accommodate the tool.

12. The system of claim 9 further including means adapted for detachable connection to the tubular tissue structure.

13. The system of claim 12 further comprising tension means for maintaining tension on the tissue structure in the direction of the proximal end of the body portion when the connection means is connected to the tissue structure.

14. The system of claim 9 further including a housing through which the elongated body portion is advanced or retracted.

15. The system of claim 14 further including body portion advancement means for advancing or retracting the body portion through the housing.

16. The system of claim 9 further comprising means for dissecting the tissue structure from surrounding tissue.

17. The system of claim 16 further comprising means for advancing or retracting the dissection means through the at least one lumen.

18. The system of claim 17 further comprising clutch means for preventing the advancement of the dissection element if a predetermined amount of resistance is encountered.

19. The system of claim 16 further comprising means adapted for detachable connection to the tubular tissue structure.

20. The system of claim 19 further comprising means operably affixed to the connection means for maintaining tension on the tissue structure in the direction of the proximal end of the body portion when the connection means is connected to the tissue structure.

21. The system of claim 20 further comprising a housing through which the elongated body portion is advanced or retracted.

22. The system of claim 21 further comprising means for advancing or retracting the body portion through the housing.

23. The system of claim 22 further comprising means for advancing or retracting the dissection means through the at least one lumen.

24. A system for removing a generally cylindrical tissue structure from a human or animal body comprising a tool having a distal operative tip for performing at least one of cutting a side branch of the tissue structure vessel, cutting the tissue structure vessel, applying a ligation clip to a side branch of the tissue structure, applying ligation clip to the tissue structure and removing body fluids, an elongated body portion having a distal end and a proximal end, the body portion having first and second lumens extending longitudinally therethrough, the first lumen being sized to accommodate the tissue structure and the second lumen being sized to accommodate the tool used in removing the tissue structure the first and second lumens being substantially separate so that the tissue structure is isolated from the tool through a substantial portion of the body portion.

25. The system of claim 24 further comprising means for viewing as area adjacent the distal end of the body portion.

26. The system of claim 24 wherein the elongated body portion includes a third lumen extending longitudinally therethrough, the third lumen being sized to accommodate the tool used in removing the tissue structure.

27. The system of claim 24 further including a tissue attachment member adapted for detachable connection to the tissue structure, the attachment member being sized to fit within the first lumen.

28. The system of claim 27 further comprising a tension element having a distal end connected to the attachment member for maintaining tension on the tissue structure in the direction of the proximal end of the body portion when the attachment member is connected to the tissue structure.

29. The system of claim 24 further including a housing through which the elongated body portion is advanced or retracted.

30. The system of claim 29 further including a body portion advancement member operably connected to the body portion for advancing or retracting the body portion through the housing.

31. The system of claim 24 further comprising a dissection element having a distal tip including an annular portion, the annular portion being located distally of the distal end of the body portion and being operative to dissect the tissue structure from surrounding tissue as the annular portion is advanced along the exterior of the tissue structure.

32. The system of claim 31 wherein the dissection element is accommodated within the first lumen of the body portion.

33. The system of claim 32 further comprising a dissection element advancement member operably connected to the dissection element for advancing or retracting the dissection element through the first lumen.

34. The system of claim 33 further comprising a clutch element to prevent advancement of the dissection element if a predetermined amount of resistance is encountered.

35. The system of claim 32 further comprising an attachment member adapted for detachable connection to the tissue structure, the attachment member being sized to fit within the first lumen.

36. The system of claim 35 further comprising a tension element having a distal end connected to the attachment member for maintaining tension on the tissue structure in the direction of the proximal end of the body portion when the attachment member is connected to the tissue structure.

37. The system of claim 35 further comprising a housing through which the elongated body portion is advanced or retracted.

38. The system of claim 37 further comprising a body portion advancement member operably connected to the body portion for advancing or retracting the body portion through the housing.

39. The system of claim 38 further comprising a dissection element advancement member operably connected to the dissection element for advancing or retracting the dissection element through the first lumen.

40. The system of claim 39 further comprising a clutch element to prevent advancement of the dissection element if a predetermined amount of resistance is encountered.

\* \* \* \* \*